United States Patent [19]

LeMay

[11] 4,137,775
[45] Feb. 6, 1979

[54] ULTRASONIC APPARATUS

[75] Inventor: Christopher A. G. LeMay, Osterley, England

[73] Assignee: Emi Limited, Middlesex, England

[21] Appl. No.: 727,128

[22] Filed: Sep. 27, 1976

[30] Foreign Application Priority Data

Oct. 2, 1975 [GB] United Kingdom ............... 40283/75
Aug. 4, 1976 [GB] United Kingdom ............... 32434/76
Sep. 15, 1976 [GB] United Kingdom ............... 38155/76

[51] Int. Cl.² .......................................... G01N 29/04
[52] U.S. Cl. ..................................... 73/602; 73/614; 73/620; 73/626; 128/2 V
[58] Field of Search .................. 73/67.5 R, 67.6, 67.7, 73/67.8 R, 67.8 S, 67.9, 602, 620, 626, 596; 128/2 V; 250/264, 272, 312, 321, 358, 360, 336, 363, 366; 340/5 MP

[56] References Cited

U.S. PATENT DOCUMENTS

| | | | |
|---|---|---|---|
| 3,673,394 | 6/1972 | Hartmann | 250/312 X |
| 3,778,614 | 12/1973 | Hounsfield | 250/362 |
| 3,789,833 | 2/1974 | Bom | 73/67.7 X |
| 3,885,224 | 5/1975 | Klahr | 73/67.85 X |
| 3,924,129 | 12/1975 | Le May | 250/336 |
| 3,939,696 | 2/1976 | Kossoff | 73/67.8 S |
| 4,074,564 | 2/1978 | Anderson | 73/596 |

OTHER PUBLICATIONS

Acoustical Holography, vol. 6, Symposium Proceedings, Pub. 1975, Plenum Press, "Algebraic Reconstruction of Spatial Distribution, etc.", —P71-90, Greenleaf et al.

Primary Examiner—Richard C. Queisser
Assistant Examiner—John P. Beauchamp
Attorney, Agent, or Firm—Cooper, Dunham, Clark, Griffin & Moran

[57] ABSTRACT

In an ultrasonic investigating apparatus a transducer can receive reflections from points in the body for which the position in one direction is relatively well known as a result of accurate range gating but for which the position in another direction is relatively less known in view of the relatively wide ultrasound beams used. Thus the reflections are only known as originating from lines in the body. These line integrals of reflection of ultrasonic energy are processed by methods appropriate to line integrals in general, as known for line integrals of X-ray absorption for example, to more accurately position the reflecting points in the body. A propagation velocity distribution can also be determined for the body to further improve the accuracy.

20 Claims, 9 Drawing Figures

ULTRASONIC APPARATUS

The present invention relates to arrangements for examining a body by means of ultrasonic energy and is especially, though not exclusively, related to such arrangements for examining living bodies for medical purposes.

In a known ultrasonic examining arrangement a piezo-electric crystal is arranged to direct a plane wave of ultrasonic energy into the body. In view of the dimensions of the crystal the plane wave tends to form a beam which can be directed through a desired region of the body. The energy is reflected from discontinuities in the body and detected at a detecting crystal which may also be the source crystal. If the energy is pulsed the position of the discontinuities can be determined by timing of the returned pulses. The position of the source and the elapsed time of the returned pulse are typically used to control the scan of a storage tube so as to position a spot, of intensity related to intensity of the returned signal, in a position relating to the position of the related discontinuity in the body. In view of the limitations of accuracy imposed by wavelength considerations, typically 0.7mm at 1MHz, this latter position can be determined to that order in the direction of the beam. However, it is only known to typically 5 – 10 mm perpendicular to that direction, in view of the width of the beam. For that reason the received signal is only known to relate to a line, 1 or 2 cm long, perpendicular to the direction of the beam.

It is an object of the present invention to provide a processing arrangement, for ultrasonic apparatus, capable of greater resolution.

According to the invention there is provided an apparatus for examining a body by means of ultrasonic energy including ultrasonic transducer means comprising at least one transducer arranged to direct ultrasonic energy through a region of the body along a plurality of beam paths at different orientations therein and to receive ultrasonic energy reflected from locations within the body to provide output signals representing line integrals of reflection of said energy towards a receiving transducer for respective lines of reflecting locations in said body and means for processing the said output signals by a method, suitable for processing line integrals of a quantity to give a distribution of the said quantity, to provide a distribution of reflection coefficients in the said region.

In order that the invention may be clearly understood and readily carried into effect an example thereof will now be described with reference to the accompanying drawings of which:

Figure 3:
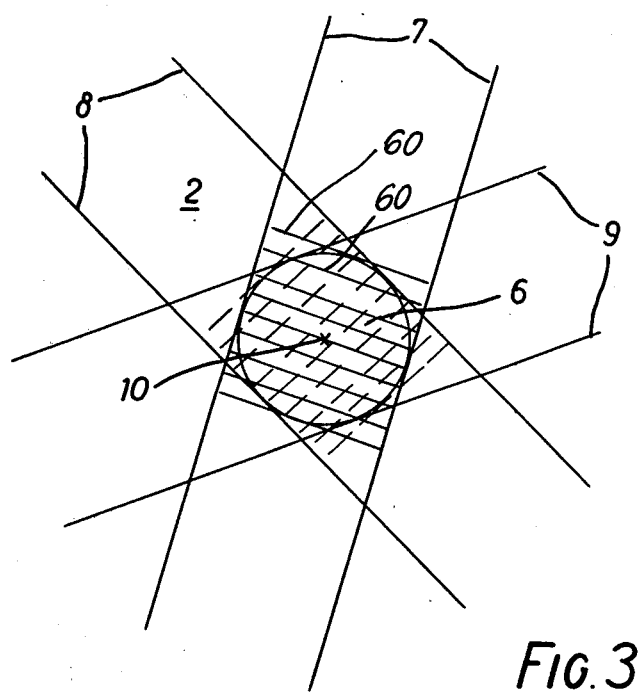
Figure 4:
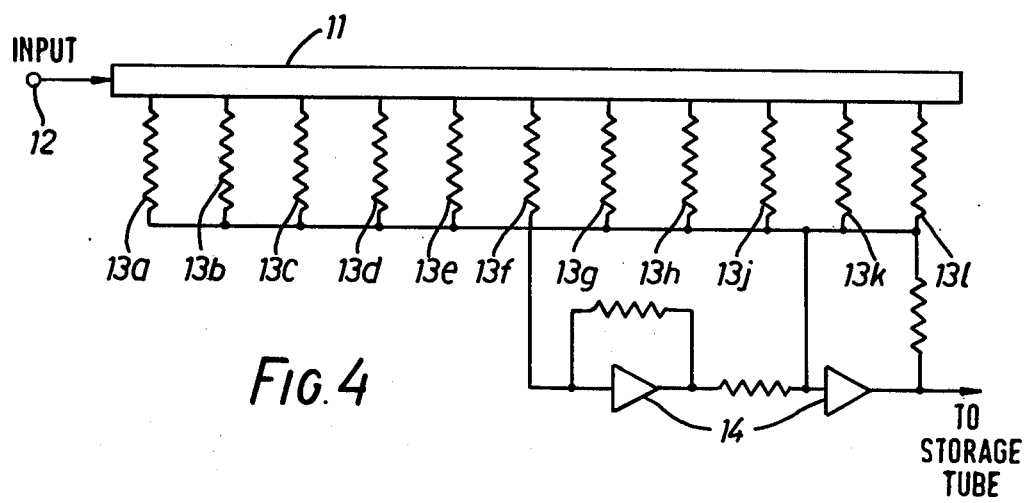
Figure 5:
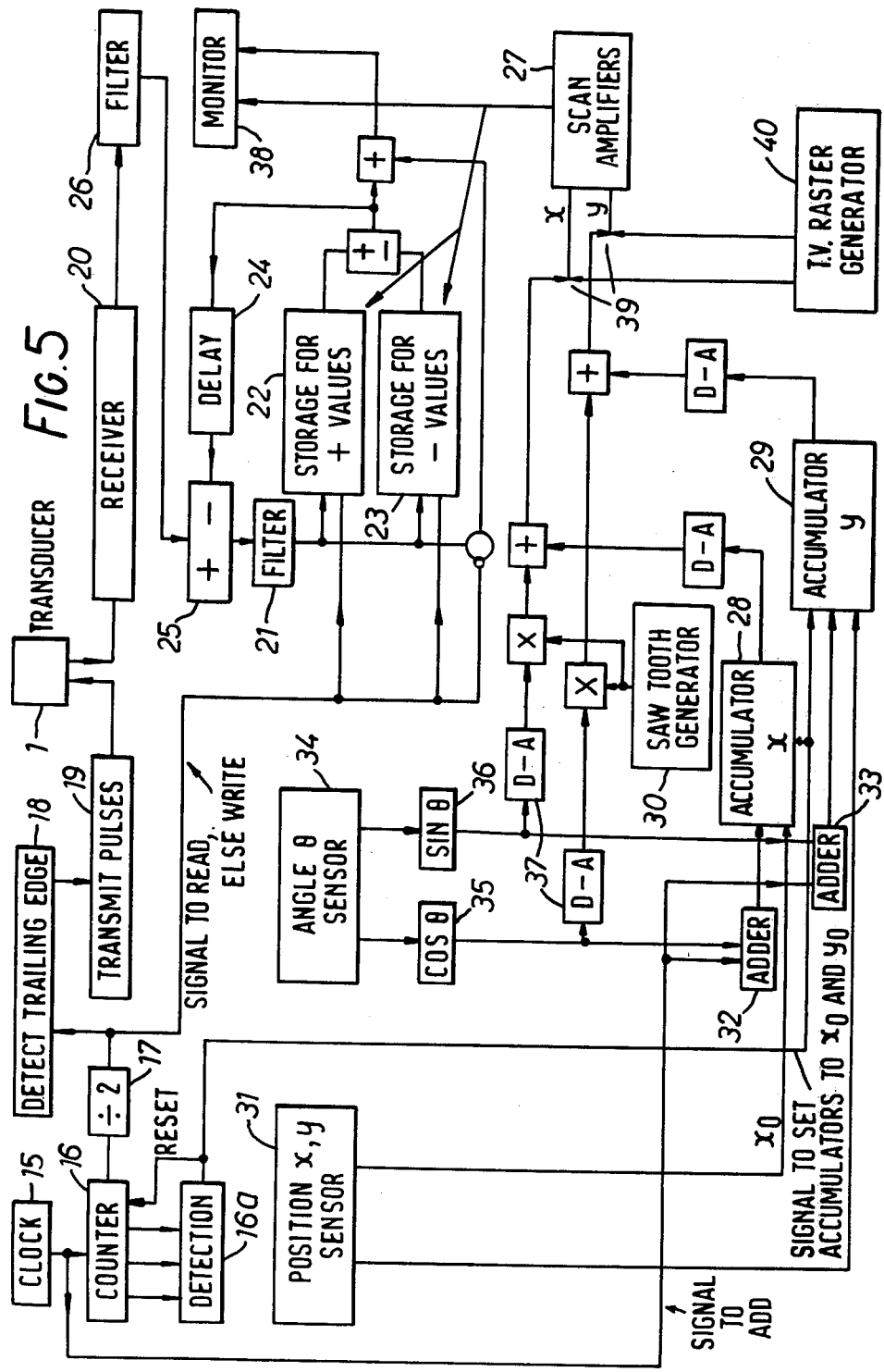
Figure 6:
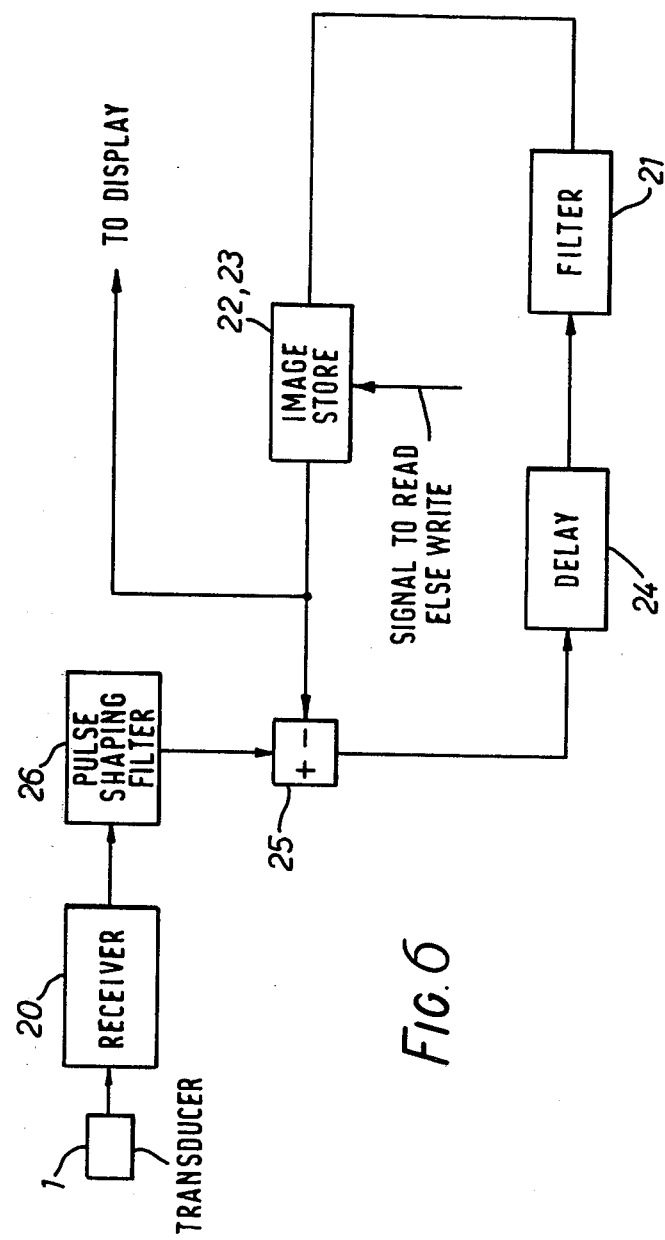
Figure 7:
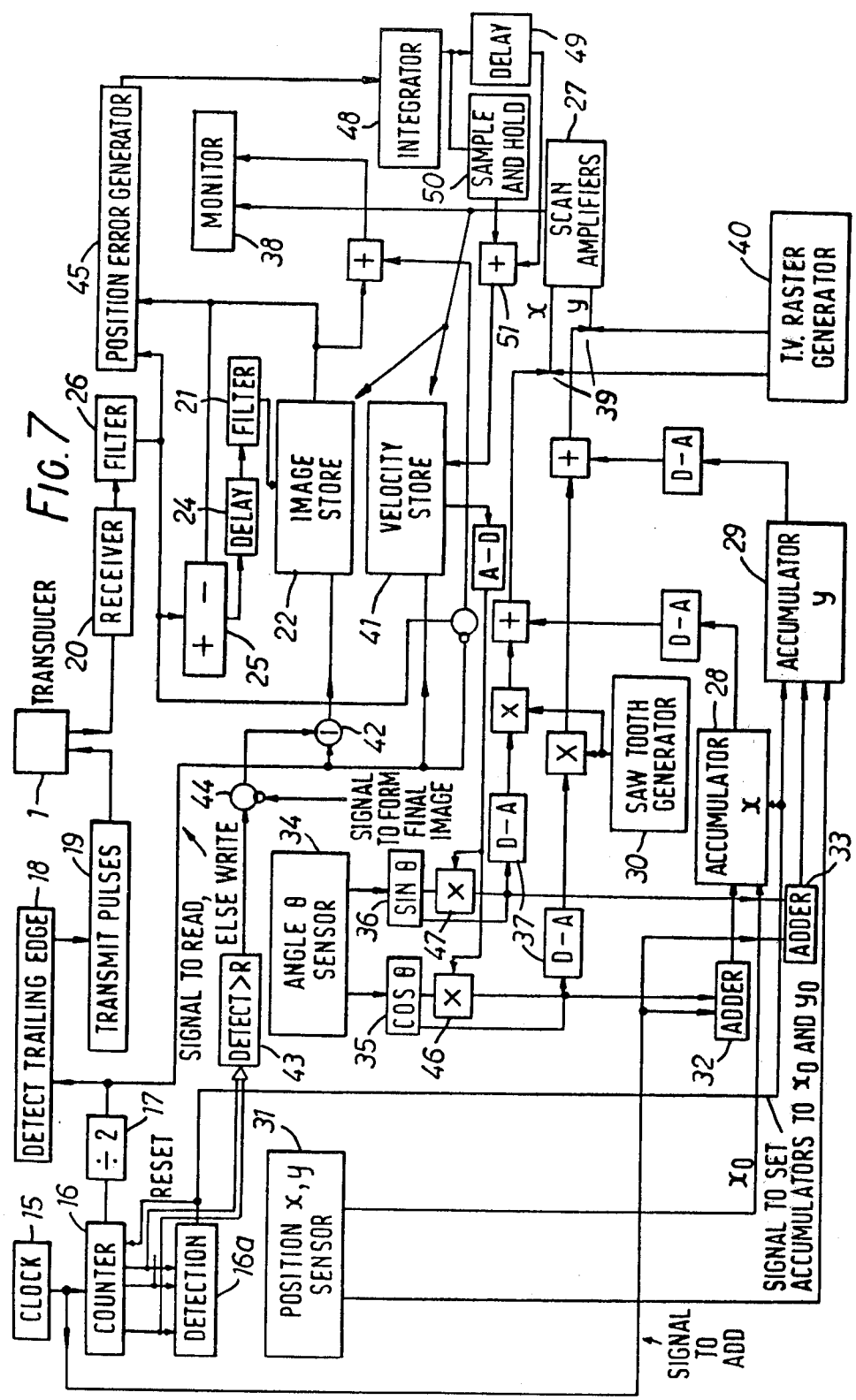
Figure 8:
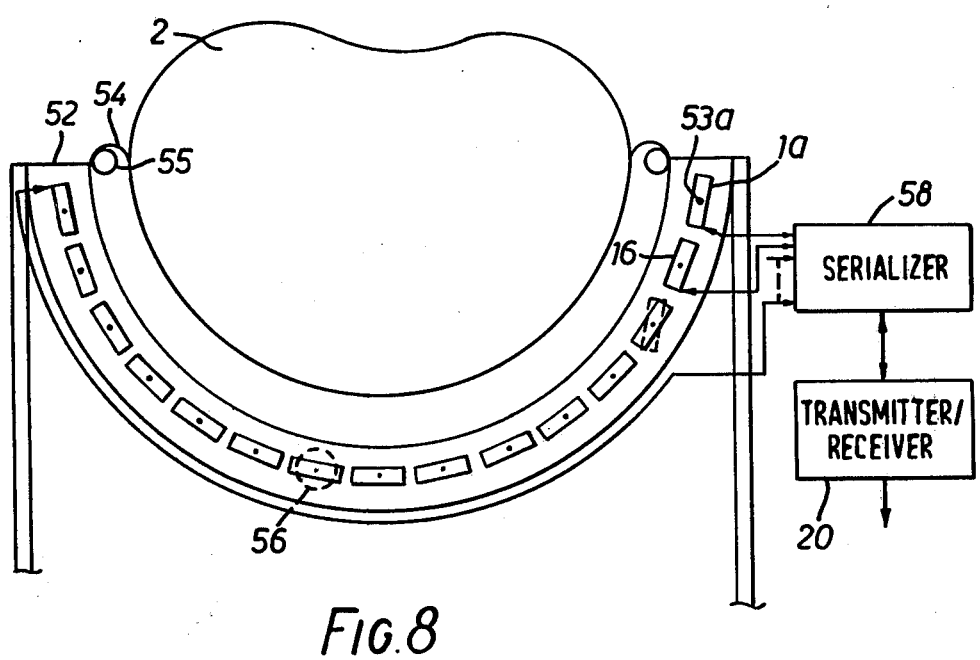
Figure 8A:
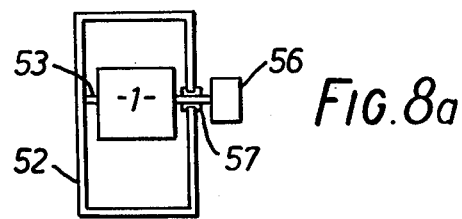

FIG. 3 shows the arrangement of such lines in relation to overlapping ultrasound beams, FIG. 4 shows a suitable convolution circuit for the invention, FIG. 5 illustrates a block diagrammatic circuit for implementing the invention, FIG. 6 shows a variation of part of the circuit of FIG. 5, FIG. 7 shows a development of the circuit of FIG. 5 including correction for varying propagation velocities and FIGS. 8 and 8a illustrate an advanced ultrasonic examining apparatus.

The apparatus may be of the type referred to hereinbefore although the invention is applicable to other arrangements and to other display techniques. The ultrasonic beam is required to insonify the body in a plurality of directions. For that purpose a source of the beam may be arranged to change its inclination at one position on the surface of the body, to direct the beam along paths disposed in a substantially planar fan shaped spread and to change the position on the surface of the body in the plane of the said fan shaped spread to provide the fan of beams from different directions.

Figure 1:
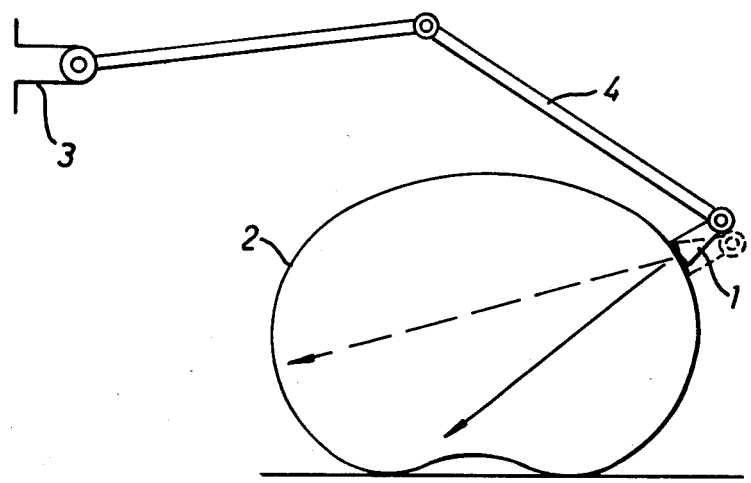
FIG. 1 shows a known ultrasonic examination arrangement.

A typical arrangement used for such purposes is shown in simplified form in FIG. 1. A source and detector transducer 1 is placed in contact with the body 2 of the patient, shown in traverse section, so as to make an acceptable acoustic contact with the skin. The transducer 1 is connected to equipment 3, which may include associated equipment, by a jointed arm 4. Arm 4 is arranged in well known manner to provide signals indicative of movements thereof so as to indicate at all times the position of the transducer 1 in relation to a fixed reference. The transducer 1 can be rocked to direct the acoustic energy from different directions, as shown, and moved across the surface of the body. The transducer is normally moved by hand, arm 4 being counterbalanced to exert no force on the body. It is of course desirable to insonify the body from a sufficient number of directions in a time short enough to reduce the risk of body movements. However small movements can be tolerated especially since surface motion will tend to be detected by movement of arm 4 and partly accounted for by the processing.

Figure 2:
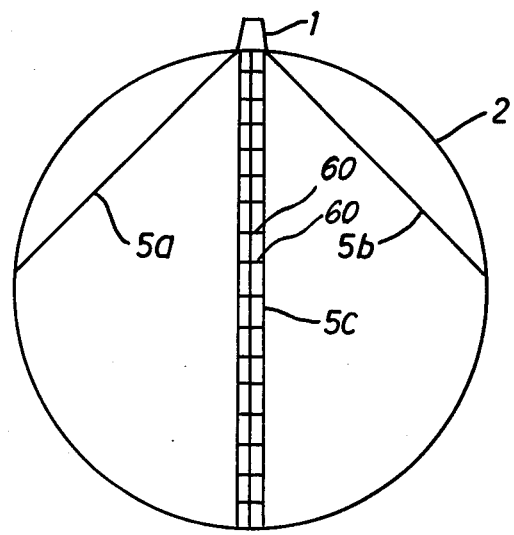
FIG. 2 illustrates the disposition of lines of scattering points in a body.

FIG. 2 is a schematic diagram which illustrates, for one position of source 1 the range of beam paths extending from 5a to 5b within a fan shaped region. For each output pulse of ultrasonic energy a series of echo pulses are received at different ranges as determined by conventional range gating. As mentioned hereinbefore, each pulse represents a reflection from a position which is only known to be on a line substantially perpendicular to the mean direction of the beam and of length determined by the effective width of the beam. Some lines of this form are indicated in FIG. 2 at 60 although in practice there would be a greater number of more closely spaced lines. For construction of a representation of the body the data signals, representing echo pulses, are used to modulate an electron beam being scanned over the target of a suitable storage tube.

The lines scanned on the tube are at positions corresponding to the positions of the notional lines 60 of reflection in the body and are of intensity determined by the total ultrasonic energy scattered in the direction of the detector transducer from the corresponding line of reflection. It will be appreciated that the beam will become relatively divergent for signal components of lower frequencies but in practice the arrangement can be considered only in terms of these components which remain on a relatively narrow beam.

A simple estimate of the reflection from any reflecting position (sometimes referred to as a point despite the fact that it must have some area in order to reflect may be obtained by combining the data for all lines 60 passing through that position or point, as a so-called layergram. It will be apparent that this effect can be achieved by writing all such lines on the storage tube, or alternatively into proper locations of a store such as a digital store. However since each line passes through several points any value obtained for one point will be in error unless that value is corrected to take account of reflection by other points thereon. This may be achieved by the use of other lines which pass through the other points but not through that being evaluated.

In U.S. Pat. No. 3,924,129 there is described a convolution method of processing data from a scanning X-ray apparatus. In that patent the data relate to the integrals of X-ray absorption along each of a plurality of X-ray paths through a body. The paths are typically arranged in sets of parallel paths. The data value for each individual path is modified by convolving the data for its respective set with a convolving series of individual terms centred on the value being modified. The effect is such that the modified values can then be superimposed as a corrected layergram to form an image in the manner described in the said U.S. Pat. No. 3,924,129 to give a distribution of X-ray absorption through the body.

To the extent that, in the present ultrasonic arrangement, the data represent the total scattering, in one direction, by reflecting positions which are along respective lines such as 60 which are closed to being straight and parallel, it will be seen that the situation is in some ways analogous to that of the said U.S. Pat. No. 3,924,129. It is therefore proposed to convolve the reflection data for reflecting positions which are along such lines with the series of terms as described in the said U.S. Pat. No. 3,924,129 so that the modified data may be applied to the store or storage tube, distributed along the appropriate line of storage locations in the store or on the storage tube, to give an improved representation of scattering points in the body.

It will be understood that instead of the convolution processing mentioned any other processing appropriate to the integrals of X-ray absorption may also be used for the present lines of ultrasonic scattering.

Lines such as 60 are relatively short in relation to the dimensions of the body compared with the longer paths of X-ray absorption in the related system. Assuming the length of a line 60 to be ten times its width then a line every 1/10 radian passing through a point over a 180° scan will give a reasonable convolution for a reflecting position or point although less may suffice. It is therefore only necessary to use a limited number of lines 60 say 32, through each reflecting position for which there is a point of the reconstructed image. It should also be noted that the nature of the convolution process is such that all parallel sets convolved to evaluate one point in the final representation should cover substantially the same area of the body. In view of the limited length of the present lines 60 which, rather than extending over a complete region of interest as in the X-ray case, are limited by the beam width of the ultrasonic beam, the area of intersection is small. FIG. 3 shows the limited, approximately circular, region 6 defined by three beams 7, 8 and 9 centred on a reflecting position or point 10. The parallel lines on which reflecting position lie are shown for beam 8 in dashed lines and it can be seen that a limited number, 9 as shown, fall in region 6. For that reason the convolution series is restricted to involve only a small number of lines, typically five, each side of the line intersecting the evaluation point 10.

FIG. 4 shows a circuit which can be used to perform the convolution directly on the echo signal data as required although, for example, a recirculating delay line can be used. The circuit of FIG. 4 comprises a delay line 11 to which the data pulse signals are applied at 12 as received.

Outputs from successive stages are taken via a series of resistors 13a to 13l to a pair of feedback amplifiers indicated at 14 and hence to the store or storage tube. Each amplifier inverts the signals of the centre of the delay line, corresponding to the centre of the convolution series, from resistor 13f and the second amplifier inverts the outputs from the other resistors. The resistors have conductivities in proportion to the terms of the convolution series so that the output at each pulse signal represents the value, modified by the convolution, for that signal which has reached the centre stage of the delay line. Alternative arrangements of positive and negative terms and appropriate resistor conductivities may be arranged to correspond to any suitable convolution series desired. It should be noted that the convolution series may be arranged to provide additional correction, for example, for the frequency characteristic of the ultrasonic transducer 1.

The invention may be applied to systems in which the source of ultrasonic energy and the receiving transducer are not coincident but are scanned independently, provided the lines such as 60 in FIG. 1 are correctly related to lines located on the storage tube. The scanning of source and detector should be in either case so that sets of such lines are provided, for all regions of the body to be examined, at suitable angular spacing, preferably less than 1/10th radian, over the widest range of angles possible to achieve the optimum result. Preferably the lines should be placed on the storage tube at their correct positions. The distribution of the modified data along the lines may also be weighted in accordance with the intensity distribution of the ultrasonic beam.

Although the data are applied to the storage tube along the line discussed the tube may be scanned in conventional television manner to derive the finally accumulated data for display.

It will be understood furthermore that instead of the single storage tube referred to, which is capable of storing both positive and negative data, conventional storage tubes may be used provided one stores the positive and the other stores the negative data.

Preferably the detector should collect all of the energy reflected by the beams at discontinuities to properly determine their positions. It should also be noted that changes in the propagation velocity along the beam path can cause errors in the determination of the positions of such discontinuities. Their positions may however be more accurately determined if that velocity is measured. Such measurement will be further discussed hereinafter.

One example of a circuit for implementation of the invention is shown in FIG. 5. A clock 15 is arranged to supply pulses at, say, 1MHz to counter 16 which counts up to 512 and then returns to zero. This may be achieved by means such as a detector 16a which detects the count 512 and resets counter 16. A binary divider stage 17 provides square pulses lasting about a half millisecond. A trailing edge detector 18 and a cooperating pulse transmitter 19 cause pulses to be sent to the transducer 1 corresponding to the trailing edge of the pulse from divider 17. During the 512μsec following each pulse a receiver 20, cooperating with transducer 1 passes the received signals via a filter 21, which is similar to that of FIG. 4, to the storage tube. Preferably receiver 20 includes a swept-gain amplifier operated such that signals received from greater range are increasingly amplified to correct for greater attenuation of their longer paths through the body. In this example two storage tubes, 22 and 23 are provided for positive and negative values respectively. At that stage any signals already stored are circulated via a delay 24 and subtracted in unit 25.

Preferably a filter 26 is also included after receiver 20 to serve as a pulse shaping filter and to integrate the output of the receiver over a period sufficient to provide a suitable count. This unit provides an output, for reflection from an object of dimension similar to one element of the final picture, which has a flat frequency spectrum over the widest range of frequencies.

In an alternative arrangement filter 21 could have been placed prior to unit 25 so that all signals entering the delayed recirculating network were already convolved or otherwise processed for 'layergram' purposes. The negative feedback of this data via delay 24 is arranged to subtract stored convolved data for each line with input convolved data and thus cause a partial cancellation of the lines of reflection on the storage tube except for those points which are reinforced with successive inputs and which, therefore represent the true points of reflection of the ultrasonic pulses for display on a suitable monitor. However it should be noted that the convolved data are not actually of the same nature as the recirculated data, for the same line, which are sums for previously evaluated points on the line.

The arrangement of FIG. 5 is therefore preferred to ensure that the data differenced are of the same nature. Unit 25 now provides the difference between the incoming 'line integral' signal and the projection of the image already held in store along the same line. If the image already held in store correctly reproduces the body being examined this difference will be zero, with the exception of random noise, and the stored image will not be altered. Otherwise, however, the difference is convolved, or otherwise processed, and added to the data held in store to further correct the image.

It will be observed that, in this case, the convolved 'line integrals' are only sufficient for correction of the already stored image to the extent that it is observed to be deficient. As soon as the image is found to be correct the processing is, in effect, stopped automatically. The processing can, of course, be stopped when the differences are reduced to a predetermined level which may be greater than zero.

Of course the feedback-delay loop can be omitted if desired so that the picture in store is built up directly from convolved or otherwise processed 'line integrals'. This would merely result in a longer total processing time without the benefit of negative feedback correction.

It should be noted that the amplitude of the final picture in stores 32 and 23 is set by the amplitude of the signal provided to unit 25. A suitable control can be provided in the receiver to adjust this amplitude as desired. Attenuation in the filter 21 provides loop gain for the feedback. At a low level of this gain stability can be assured and noise on the image reduced at the expense of a larger processing time.

FIG. 6 shows in simplified form an alternative arrangement, for the feedback loop, which is more tolerant of possible errors in the delay line 24. In this arrangement the output of unit 25 is directly differenced with the output of stores 22, 23, the differenced values being then delayed and convolved or otherwise processed. This ensures that any frequencies attenuated in the delay line will only be attenuated after the differencing. They will thus be more slowly built into the image but will ultimately reach their correct values, provided there is not excessive phase shift.

Returning now to the circuit of FIG. 5, the scan waveform of the storage tubes, and a display monitor are controlled by scan amplifiers 27 which are supplied with the sum of a linear function, from accumulators 28 and 29, and the output from a saw tooth generator 30. The sum is arranged to provide short lines closely spaced at right angles to the beam path, which is indicated by changing values of parameters x and y. These parameters indicate the position of the transducer and are derived from a sensor 31.

Pulses from the clock 15 cause numbers to be added to the accumulators 28 and 29 via adders 32 and 33. The numbers represent the x and y velocities of the sweep derived from the angular position $\theta$ of the transducer by sensor 34. Unit 35 derives the cosine of $\theta$ and unit 36 the sine of $\theta$.

The beam path can be calculated digitally by this means since it moves relatively slowly. The smaller scan lines at right angles are derived by the same general principle but by analogue means to obtain speed rather than accuracy. Digital to analogue coverters 37 provide the cos and sine terms to multipliers where they are multiplied by the analogue saw tooth term. It should be noted that if the cosine generator supplies the accumulator 28 for x then it must also supply the multiplier which feeds the y input into the scan amplifier and vice-versa.

A display monitor 38 takes the output from the storage tubes and the receiver alternatively during the acquisition modes. On completion of storage a switch 39 is transferred to connect a T.V. raster generator 40 instead of the special scan representing the beam paths. Thus the entire image is displayed.

The apparatus described in relation to FIG. 5 operates in a similar manner to conventional ultrasonic echo apparatus to the extent that it is used in a manner which assumes a constant average propagation velocity, for the ultrasonic energy, to estimate the origin of each echo from its time of travel. However, since bodies are not completely homogeneous such an assumption can lead to errors. As noted hereinbefore it is preferable to evaluate to some extent the actual propagation velocities in deriving the final representation.

It has been suggested (Greenleaf, Johnson, Samayoa and Duck, Proceedings of Symposium held February 1975, published in "Acoustical Holography" Vol 6 pp 71-9, Plenum Press, London and New York) that the velocity of ultrasonic echo pulses, in elemental areas of a body, can be determined. Thus a 'map' of ultrasonic velocities in a region of interest can be provided. For that purpose any suitable ultrasonic echo apparatus can be used, including that described hereinbefore.

A suitable procedure for velocity mapping can be as follows. Initially a representation is derived for a limited distance from the surface of the body. This may be selected from echo data previously obtained for the entire body or may be derived from a limited examination including a range gate to limit the depth from which echoes can be received. This limited region examined will usually include at least some fairly distinct features, for example the patient's skin, which, since they are at or near to the surface, can be positioned with reasonable accuracy despite velocity errors. As an alternative a special reflector may be placed in a known position close to the patient. From several positions about the body ultrasonic pulses are then reflected from the features or reflector, for which the position is known, and an average velocity of propagation computed for the notional line joining the transducer to the respective feature.

It will be understood that the ultrasonic pulse travelling along such a notional line travels at varying velocities through regions of different density so that the computed average velocity is in fact an integral of velocity along that line. Such line integrals are also analogous to the beam path integrals of X-ray absorption discussed hereinbefore and a sufficient quantity of these integrals, uniformly distributed, may be processed, as described in U.S. Pat. No. 3,778,614 or by a transform process such as the convolution process described in U.S. Pat. No. 3,924,129 to provide a distribution of velocities in elemental areas of the body.

It should be noted that the ultrasonic beams used tend to be relatively wide as a result of the transducers used so that the velocity map will comprise large elemental areas, say 1 centimeter square. However this is sufficient for the purpose to be described hereinafter.

As an alternative to the known scanning arrangements, described hereinbefore, which use a single transducer placed at several points against the patient's body, it may be desirable to use a fixed array of transducers surrounding the body and coupled thereto by a suitable medium. In that case the distances between different transducers, or transducer positions, will be accurately known and the required average velocities may readily be derived from transit times over those distances.

It is therefore proposed to use the velocity map, derived in any suitable manner, to more accurately determine the position of the line integrals of reflection coefficients determined by the method described hereinbefore.

In general, knowing the time of flight of the pulse, it is possible to calculate the distance, through regions of known propagation velocities, travelled by the pulse. This straightforward calculation may be performed by either analogue or digital means. However it was suggested hereinbefore that, as an alternative to digital processing, the processing can be performed by superimposition of convolved line integrals on the face of a storage tube. It will be apparent that, in such an embodiment, the velocity of the electron beam spot, in direction away from the transducer, should be related to the velocity of the ultrasonic pulse from the transducer. It is therefore proposed to control the spot velocity in the said direction in accordance with the stored velocities for the elemental regions.

FIG. 7 shows a modification of the circuit of FIG. 5 suitable for determining and using propagation velocities. The circuit is otherwise assentially the same as that of FIG. 5, except that the alternative feedback loop of FIG. 6 has been used in conjunction with a single image store 22 taking positive and negative data. Items in common with FIG. 5 have been identified by the same reference numerals.

Principally the circuit is amended to include a velocity store 41 which may also be a storage tube or other store. In this embodiment it is operated in conjunction with a range gate 42 controlled by a unit 43 which detects if the number on the counter 16 is above a predetermined value R, in which case the received signals should be rejected for the purposes of the first-stage of constructing the velocity map. An inhibit gate 44 is used by the operator to inhibit the signal not to write after the velocity map is complete so as to allow the final image to be compiled for signals at all ranges.

As an alternative a "form final image" signal can be used to activate the swept gain component of the receiver. In that case, in the initial stage, when the velocity map is being formed, the receiver 20 would have constant gain, so that only reflections from near the surface would be recorded. The velocity store would then be corrected as a second stage with final image construction as a third stage.

For operation the velocity store 41 is preset to an expected average velocity for tissue, for example by a manual 'clear' control and a velocity setting dial which have not been shown. With the range gate 42 in operation a first image is formed, as described hereinbefore, of features at limited range from the surface. In further operation signals representing reflections from the side of the body distant from the transducer are first passed to a position error generator circuit 45. These circuits can conveniently be a pattern recognition device such as that described in the specification of U.S. Pat. No. 3,727,183. The circuits 45 withdraw data, from the image store 22, stored in the first stage for the same region as the new reflection but obtained when the transducer was as the opposite side of the body. By comparing the new signal with the stored data the circuits 45 provide an error signal indicating the difference between the 'true' position as derived in the first stage and the new position derived for the longer prth across the body assuming the preset velocity.

Velocity store 41 supplies two multipliers 46 and 47 which multiply respectively the cosine and sine values from units 35 and 36. These components, as described hereinbefore, control the rate of scan of store 22 and also in this circuit of store 41 and therefore multipliers 46 and 47 adjust these values to bring the rate of scan into line with the stored velocities for the path scanned (initially the preset value). If an error signal is provided by circuits 45 it must be assumed that all points on the path scanned, up to the current position, are in error. To achieve corrections for these points all position errors from circuits 45 are integrated in an integrator circuit 48 and the integrated errors passed to store 41, via a delay 49, to be added to or subtracted from the earlier stored values for the same path, as appropriate, on the next scan, after about 1 millisecond delay. Thus a correct average velocity for that path is gradually provided in store 41.

It is desirable for the integration process to ensure that the corrections are applied to all positions up to the current position but not thereafter so that there is no correction outstanding at the end of the path. This effect can be ensured by a constant of integration. A suitable constant of integration is provided by subtracting the final value of the integral from unit 48 after the last reflection. For that purpose a sample-and-hold unit 50, controlled by detection unit 16a by a connection not shown, samples the required value and adds that value to the delayed integral at 51.

As a result of the successive modifications to the velocity store 41 the values on the adders 32 and 33 are altered and in turn alter the rate of scan of store 22. The process continues until the input reflection signals received from filter 26 line up with the stored values from store 22. No further corrections are then provided and the system is stable until the tranducer 1 is moved.

As a result of successive operations of this process a complete velocity map of the body is built up in store 41. This has in fact, as described, been formed by a process which is similar to that described for X-ray from path integrals in U.S. Pat. No. 3,778,614. However other methods, such as convolution form of processing could be used.

With the velocity map complete no further error signals are provided by circuits 45 and a signal to form the final image is given by means of gate 44 which effectively removes range gate 42. The final image formation is as described in relation to FIG. 5 with the speed of scanning of store 22 being in accordance with the velocity map stored in store 41. In this process circuits 45 may still provide further error signals as a result of minor inconsistencies in the received signals. These errors can be used to correct store 41 as before to provide suitable agreement. It should also be noted that the loop including store 22 can erase stored data which does not agree with the incoming signals. However this is a relatively slow correction and small velocity errors should be corrected before such erasure can be completed.

After sufficient operation of the entire system the final picture is sufficiently correct that no error signals are provided by circuits 45 and all new reflections are cancelled by subtractor 25 so that no further correction can take place.

It has been assumed hereinbefore that ultrasonic investigation, to provide data to be processed as described, would be carried out using a known type of hand operated transmitting and receiving transducer. It has been mentioned however that it would be advantageous to provide a fixed multi-transducer array capable of automatic operation. FIG. 8 shows one possible arrangement for such an array extending halfway around the body 2 of the patient. The array may, of course, have greater or lesser extent extending to 360° coverage.

In this example a semicircular water filled box 52 is provided. This may be independently supported as shown or may be a part of a larger bed or other support for the patient. Box 52 includes, distributed in a semicircle, detectors 1a 1b etc. and mounted so as to be capable of rotation about axes 53a etc., normal to the plane of the FIGURE.

Box 52 is open at its inner surface and a water filled bag 54, supported by rods 55 is sealed thereto to close the open side with a flexible closure giving good acoustic transmission. The patient lies, normally face down, positioning the part of the body to be examined against bag 54. Care is of course taken to exclude air pockets to ensure a good acoustic contact with the bag. Grease or suitable fluid may be used if desired to ensure such a contact.

The transducers are rotated about axes 53, to provide insonification from different directions, by means of respective motors 56. This arrangement is also illustrated in FIG. 8a, which shows an axle forming an axis 53 journalled in the walls of box 52. One end of the axle extends through the wall, via a rotary water seal 57 to the motor 56. Motor 56 includes any necessary gearing to achieve the correct control and indicator means to show the progress of the rotation for control purposes.

In operation the transducers are pulsed in succesion, the output and input pulses being directed by a serializer 58, and also rotated to send and receive acoustic energy over the required number of paths in a relatively short time. It should be noted that for this purpose detectors 1 should be placed as close together as possible. The detectors may be individually rotated as shown but may alternatively be linked by a series of belts or linkages to operate together.

What I claim is:

1. An apparatus, for examining a body by means of ultrasonic energy, including: ultrasonic transducer means, comprising at least one transmitting transducer, arranged to direct ultrasonic energy through a region of the body along a plurality of beam paths at different orientations therein; at least one receiving transducer, which may also be the transmitting transducer, arranged to receive ultrasonic energy reflected from locations within the body to provide, for each of said beam paths, a set of output signals representing line integrals of reflection of said energy towards said receiving transducer for respective lines of reflecting locations transverse to the direction of propagation of the energy; and processing means for providing a representation of the distribution of reflection coefficients in said region, the processing means including a data store representing said region and having a matrix of addresses, one for each of a plurality of elements of the body in said region, and means for distributing to the addresses, corresponding to elements intersected by each line of reflecting locations, a value related to the output signal for the respective line together with contributions derived from other output signals of the same set.

2. An aparatus according to claim 1 wherein said transducer means comprises means arranged to transmit ultrasonic energy and receive the said energy at substantially the same point after reflection.

3. An apparatus according to claim 2 wherein the said transducer means comprise a single transducer arranged to transmit and receive ultrasonic energy.

4. An apparatus according to claim 2 wherein the said lines of reflecting locations are substantially perpendicular to the mean direction of propagation of the ultrasonic energy.

5. An apparatus according to claim 1 wherein the said means for distributing includes sub-processing means arranged to subject groups of output signals of a set to a transformation process to provide the said values.

6. An apparatus according to claim 5 wherein the said sub-processing means is arranged to convolve each set of output signals or further signals derived therefrom with a convolution series of terms.

7. An apparatus according to claim 5 wherein the said means for distributing includes iteration means, cooperating with said sub-processing means, arranged to subject the said output signals to an iterative form of processing which combines with said transformation process to derive the said values.

8. An apparatus according to claim 7 wherein the said iteration means includes means arranged to compare the output signals with estimated values already stored for addresses corresponding to locations on respective lines to provide error signals indicative of differences therebetween, and to provide the error signals to the sub-processing means for processing by said transformation process, to improve the accuracy of the said distribution.

9. An apparatus according to claim 1 wherein said processing means includes means arranged to determine from at least some of said output signals a representation of the distribution of velocities of ultrasonic energy in elements of the said region.

10. An apparatus according to claim 9 wherein said processing means includes means arranged to evaluate the propagation time of the ultrasonic energy giving rise to at least some of said output signals from velocities in regions through which the energy has passed and means for utilising the propagation times to more accurately determine the positions of the lines of reflecting locations corresponding to the said output signals.

11. An apparatus, for examining a body by means of ultrasonic energy, including: ultrasonic transducer means comprising at least one transmitting transducer, arranged to direct ultrasonic energy through a region of the body along a plurality of beam paths at different orientations therein; at least one receiving transducer, which may also be the transmitting transducer, arranged to receive ultrasonic energy reflected from locations within the body to provide, for each of said beam paths, a set of output signals representing line integrals of reflection of said energy towards said receiving transducer for respective lines, of reflecting locations, transverse to the direction of propagation of the energy; means for deriving from the output signals for each beam path a modified output signal for each said line by combining, according to a predetermined weighting function, a proportion of the respective output signal for said line with proportions of the output signals for a predetermined number of lines on each side of said line; a data store representing said region and having a matrix of addresses, one for each of a plurality of elements of the body in said region; and means for distributing among the addresses, corresponding to elements intersected by each line of reflecting locations, the modified output signal for the respective line or a signal derived therefrom.

12. An apparatus according to claim 11 in which the means for deriving includes: a tapped delay line; means for applying the output signal for a beam path to the delay line input in sequence; means for weighting the output appearing at each tapping point according to said weighting function; and means for combining the weighted outputs to provide the modified output signal for the line of reflecting locations giving rise to the output signal at the centre tapping point of the line.

13. A method of examining a body by means of ultrasonic energy, including the steps of:
(a) transmitting ultrasonic energy through a region of the body along a plurality of beam paths of different orientations therein;
(b) receiving the ultrasonic energy after reflection at reflecting locations within the region and measuring the intensity of the energy received after different propagation times;
(c) defining each measurement of intensity as a line integral of reflection for a line of reflecting locations transverse to the direction of propagation of the energy for a respective beam path;
(d) notionally defining a matrix of elements in the region of the body
(e) distributing to all elements, intersected by a chosen line of reflecting locations, a value related to the line integral associated with that line together with contributions derived from other line integrals for the same beam path; and
(f) repeating step e) for substantially all lines of reflecting locations defined within the said region.

14. A method according to claim 13 in which the step of distributing the said value includes the step of convolving line integrals, or contributions derived therefrom, for the chosen line and a predetermined number of lines on each side of the chosen line, with a convolution series of terms.

15. A method according to claim 14 in which the step of distributing the said value further includes the step of comparing the line integrals, or contributions derived therefrom, with estimated values already stored for the appropriate addresses and deriving the differences between them as error signals for improving the accuracy of the said estimated values.

16. A method according to claim 15 in which the said step of convolving is performed on error signals derived from the respective line integrals.

17. A method of examining a body by means of ultrasonic energy including the steps of:
(a) directing ultrasonic energy into the body from a point at the body surface,
(b) measuring the intensity of the energy received at a point at the body surface after reflection at locations distributed within a region of the body to derive measurement signals, and determining the time of propagation of the radiation,
(c) organising the measurement signals on the basis of propagation time at suitable propagation velocities into output signals, each output signal representing a line integral of reflection of ultrasonic energy for one of a plurality of substantially parallel lines on a path traversed by the energy,
(d) repeating steps a, b and c for different points at the surface of the body to provide further output signals for other pluralities of substantially parallel lines,
(e) processing the said output signals, in sets corresponding to sets of said substantially parallel lines, by a method suitable for processing line integrals of a quantity for superimposition as a corrected layergram, and
(f) superimposing the processed output signals, as values distributed along the respective lines, in a store representing the said region to provide a representation of the distribution of scattering of the ultrasonic energy in the region.

18. A method according to claim 17 wherein the said suitable propagation velocities are estimated average propagation velocities.

19. A method according to claim 17 including the step of constructing a distribution of velocities of propagation of the energy in the said region and wherein the suitable propagation velocities are determined from the said distribution.

20. A method according to claim 19 in which the velocities of propagation of the energy in said region are evaluated by measuring the propagation times of energy reflected from features at or near the surface of the body for which a position has been determined.

* * * * *